(12) United States Patent
Nawrocki

(10) Patent No.: US 9,664,263 B2
(45) Date of Patent: May 30, 2017

(54) MOVEMENT DEVICE COMPRISING A COMBINED INDIVIDUAL MOVEMENT AND BLOCK MOVEMENT DRIVE FOR A PLURALITY OF JOINTLY GUIDED MOVEMENT UNITS

(71) Applicant: Hamilton Bonaduz AG, Bonaduz (CH)

(72) Inventor: Eduard Nawrocki, Bonaduz (CH)

(73) Assignee: HAMILTON BONADUZ AG, Bonaduz (CH)

(*) Notice: Subject to any disclaimer, the term of this patent is extended or adjusted under 35 U.S.C. 154(b) by 233 days.

(21) Appl. No.: 14/510,851

(22) Filed: Oct. 9, 2014

(65) Prior Publication Data
US 2015/0101427 A1    Apr. 16, 2015

(30) Foreign Application Priority Data
Oct. 10, 2013 (DE) .......................... 10 2013 220 427

(51) Int. Cl.
*F16H 19/06* (2006.01)
*G01N 35/10* (2006.01)
(Continued)

(52) U.S. Cl.
CPC .......... *F16H 19/06* (2013.01); *G01N 35/1067* (2013.01); *A47B 21/03* (2013.01);
(Continued)

(58) Field of Classification Search
CPC .......... G01N 35/1065; G01N 35/1083; G01N 35/1081; G01N 2035/1069;
(Continued)

(56) References Cited

U.S. PATENT DOCUMENTS 3,834,520 A * 9/1974 Patin ....................... B66B 21/12
                                                              104/25
5,425,402 A    6/1995 Pringle
(Continued)

FOREIGN PATENT DOCUMENTS

DE        EP 2402764 A1 *  1/2012    ......... G01N 35/0098
DE        102010064049 A1    6/2012
(Continued)

OTHER PUBLICATIONS

Search Report issued for European patent application No. 14168093.0 dated Apr. 14, 2015 with machine English translation, 10 pages.
(Continued)

*Primary Examiner* — William C Joyce
*Assistant Examiner* — Randell J Krug
(74) *Attorney, Agent, or Firm* — Rothwell, Figg, Ernst & Manbeck, P.C.

(57) ABSTRACT

A linear movement device comprising at least two linear movement units which are guided in a movable manner along a shared linear movement axis, wherein the linear movement device comprises a first linear drive and a second linear drive, in such a way that each linear movement unit can be driven in movement along the linear movement axis merely by the first linear drive, merely by the second linear drive, and also by both linear drives together. The first and the second linear drive are coupled to the linear movement units so as to transmit drive force, in such a way that when only one of the first linear drive and the second linear drive is activated, the linear movement units can be driven in movement in a shared direction along the linear movement axis at different speeds.

20 Claims, 3 Drawing Sheets

(51) Int. Cl.
 *A47B 1/00* (2006.01)
 *F16H 19/00* (2006.01)
 *A47B 21/03* (2006.01)
 *A47B 63/06* (2006.01)
 *A47B 57/58* (2006.01)

(52) U.S. Cl.
 CPC .............. *A47B 57/58* (2013.01); *A47B 63/06* (2013.01); *F16H 19/003* (2013.01); *G01N 35/1074* (2013.01); *G01N 35/1081* (2013.01); *G01N 2035/1069* (2013.01); *Y10T 74/18832* (2015.01)

(58) Field of Classification Search
 CPC ........ G01N 35/1074; A47B 1/00; A47B 1/10; A47B 21/02; A47B 21/03; A47B 51/00; A47B 53/02; A47B 57/58; A47B 57/585; A47B 63/06; A47B 65/10; F16H 19/06; F16H 19/003
 USPC ............... 74/89.2, 89.21, 89.22, 37; 474/148
 See application file for complete search history.

(56) References Cited

U.S. PATENT DOCUMENTS

| | | | |
|---|---|---|---|
| 5,949,681 A * | 9/1999 | Asai | H05K 13/021 29/759 |
| 5,974,904 A * | 11/1999 | Dirschbacher | B23Q 5/404 74/89.22 |
| 6,439,631 B1 | 8/2002 | Kress | |
| 2006/0088443 A1* | 4/2006 | Mattila | B25J 9/023 422/63 |
| 2012/0186367 A1 | 7/2012 | D'Amore et al. | |
| 2012/0247239 A1* | 10/2012 | Hortig | B65G 1/0407 74/89.22 |
| 2013/0233096 A1 | 9/2013 | Schlegel et al. | |

FOREIGN PATENT DOCUMENTS

| | | |
|---|---|---|
| EP | 0216026 A1 | 4/1987 |
| EP | 0289946 A2 | 11/1988 |
| EP | 2410342 A2 | 1/2012 |
| JP | H0949848 A | 2/1997 |
| JP | 2005-195452 A | 7/2005 |

OTHER PUBLICATIONS

Search Report issued for German patent application No. 10 2013 220 427.2 dated Mar. 6, 2014, with machine English translation, 9 pages.

* cited by examiner

MOVEMENT DEVICE COMPRISING A COMBINED INDIVIDUAL MOVEMENT AND BLOCK MOVEMENT DRIVE FOR A PLURALITY OF JOINTLY GUIDED MOVEMENT UNITS

CROSS REFERENCE TO RELATED APPLICATION(S)

This application claims priority to German Application No. 10 2013 220 427.2, filed Oct. 10, 2013, the entire contents of which are incorporated herein by reference.

BACKGROUND

Field of the Invention

The present invention relates to a linear movement device comprising two or more linear movement units which are guided in a movable manner along a shared linear movement axis.

Background of the Invention

The linear movement device comprises a combined block- and individual drive, which is configured to move the two or more linear movement units both jointly as a block along the linear movement axis—in other words without movement relative to one another—and with movement relative to one another along the linear movement axis.

The linear movement units are preferably supports of pipetting ducts and thus part of a pipetting device. The present invention therefore also relates to a pipetting device comprising a linear movement device as disclosed in the following.

A block- and individual drive device of this type is known on pipetting devices comprising a plurality of pipetting ducts which can be moved both individually, separately from one another, and jointly in a block.

Deviating from the above-defined conventional combined block- and individual drive device, individually linear-motor-driven pipetting ducts are also known, each of which comprises a separately operable rotor, a plurality or even all of the rotors running on a shared stator. These pipetting ducts, or generally speaking these linear movement units, can be driven in a block or individually by different modes of operation of the linear-motor drives.

The subsequently published DE 10 2012 216 544.4 further discloses a combined block- and individual drive device in which a block movement transmission gear unit comprises a drive spindle extending parallel to the linear movement axis and in which each linear movement unit further comprises a spindle nut passed through by the drive spindle. In a manner known per se, in this case the linear movement units can be moved jointly as a block relative to the drive spindle along the drive spindle longitudinal axis by rotating the drive spindle about the drive spindle longitudinal axis thereof relative to the individual spindle nuts. By way of a separate drive shaft, comprising sliding blocks which are mounted rotationally engaged but axially displaceable thereon and which are in meshed engagement with the spindle nuts and coupled to the linear movement units, the linear movement units can be moved along the linear movement axis with movement relative to one another.

Combined block- and individual drive devices are advantageous in particular on pipetting devices in which pipetting ducts, arranged in succession along the movement path or linear movement axis, as the linear movement units can be moved along the movement path as a jointly movable block at a predetermined distance, without a relative change in distance. In some cases, it may be necessary to change the distance along the movement path between the individual pipetting ducts, or generally speaking the linear movement units, for example if liquid is to be pipetted out of or into a titre plate in which depressions for receiving liquid, generally known as "wells", are at a different distance from one another from in other titre plates which are processed using the same pipetting device at different times. Individual movement of this type of the pipetting ducts, or generally speaking linear movement units, to change the distance between them along the movement path, is also referred to as "spreading movement" in the present application.

SUMMARY OF THE INVENTION

The object of the present invention is to provide a linear movement device of the aforementioned type which can both drive the two or more linear movement units in movement as a block, without any speed relative to one another along the shared linear movement axis, and drive the two or more linear movement units in movement, with a speed relative to one another in movement along the linear movement axis, using merely two linear drives.

In accordance with a first general inventive concept, this object is achieved by a linear movement device comprising at least two linear movement units which are guided in a movable manner along a shared linear movement axis, the linear movement device comprising a first linear drive and a second linear drive, in such a way that each linear movement unit can be driven in movement along the linear movement axis merely by the first linear drive, merely by the second linear drive, and also by both linear drives together, the first and the second linear drive being coupled to the linear movement units so as to transmit drive force, in such a way that when merely the first linear drive or merely the second linear drive is activated the linear movement units can be driven in movement in a shared direction along the linear movement axis with a speed relative to one another, whereas when the first and the second linear drives are activated simultaneously all of the linear drive units can be driven at least in joint movement in the same direction along the linear movement axis without any speed relative to one another.

It is preferred for the linear drive axis to describe a straight-line path, within the strict mathematical meaning of an axis. However, it is not intended to exclude the possibility that the linear movement axis extends in a singly or repeatedly curved path, in such a way that "linear movement axis", in the most general meaning thereof, means any desired movement path.

In principle, it is not intended to exclude the possibility that more than the two aforementioned linear drives are provided on a linear movement device. However, the invention is particularly advantageous, since it is being achieved with the minimum possible number of linear drives, if the linear drive device comprises exactly two linear drives.

In this case, each of the two aforementioned linear drives, taken individually, is coupled to the two or more linear movement units, in such a way that if merely the first or merely the second linear drive is activated and the respective other linear drive is not activated, the two or more linear movement drives move jointly in the same direction along the linear movement axis, but have different absolute speeds with respect to a coordinate system which is fixed with respect to the guide or frame and which is stationary relative to a linear guide guiding the linear movement units along the linear movement axis. In other words, in this type of drive the two or more linear movement units have a speed relative to one another. This mode of operation is referred to in the following as "individual movement".

However, if the first and the second linear drives are activated simultaneously in a predetermined manner, the two or more linear movement units can be driven in joint movement in a shared movement direction along the linear movement axis at the same absolute speed in each case, in other words without any speed relative to one another. This mode of operation of a movement drive, without any speed of the linear movement units relative to one another, is referred to in the following as "block movement" or the like. This is not intended to exclude the possibility that the linear movement units can also be driven in movement other than that denoted as a block movement, in the same direction at the same speed, when both the first and the second linear drive are activated simultaneously. In any case, it should be possible to bring about this block movement by activating the two linear drives simultaneously.

In addition to the aforementioned individual movement mode of operation and the aforementioned block movement mode of operation, it may be provided that at least all but one of the linear movement units can be driven in movement with a speed relative to another along the linear movement axis, depending on the respective operating state of the two linear drives.

Since, as disclosed above, the two or more linear movement units can be driven in individual movement, in other words in movement along the linear movement axis with a speed relative to one another, both by the first and by the second linear drive, the two linear drives may be operated in such a way that for exactly one linear movement unit of the two or more linear movement units the drive movements transmitted by the two linear drives cancel each other out. This linear movement unit, to which the cancellation condition for the drive movements applies, is thus stationary relative to the coordinate system fixed with respect to the guide and thus relative to the linear guide of the linear movement units, whilst all of the other linear movement units have a speed relative to the stationary linear movement unit and relative to the remaining linear movement units.

By selecting the operating parameters of the two activated linear drives appropriately, a theoretical stationary point, at which the drive movements transmitted by the two linear drives cancel each other out, may be a theoretical location positioned between the linear movement units, in such a way that not only all but one of the linear movement units, but actually all of the linear movement units, can be driven in movement with a speed relative to one another along the linear movement axis. In this case, irrespective of the position of the stationary point, linear movement units on axially different sides of the stationary point can have absolute speeds in different directions, for example towards or away from the stationary point.

Likewise, by selecting the transmission of drive movement from the linear drives to the linear movement units appropriately, a mode of operation of the two linear drives may be provided in which the drive movements transmitted from each individual linear drive to each individual linear movement unit add up to equally large drive movements for all of the linear movement units, in such a way that in this case all of the linear drive units can be driven in movement without a speed relative to one another along the linear movement axis. This is the aforementioned block movement operation.

Thus, when the first and the second linear drive are activated simultaneously, depending on the selection of the operating parameters of the linear drives, the linear movement units can be driven in movement without a speed relative to one another in a shared direction (block operation) or in movement with a speed relative to one another in a shared direction (individual operation to achieve a spreading movement), or one set of the two or more linear movement units can be driven in movement in a first direction and a second set of the at least two linear movement units can be driven in movement in a direction counter to the first direction along the linear movement axis. Since, as disclosed above, a linear movement unit can be selected as the stationary linear movement unit by appropriately selecting the operating parameters of the two linear drives, the total of the first set and second set of linear movement units need not necessarily give the total number of linear movement units. For example, the first set may move towards or away from the stationary linear movement unit and the second set may move towards or away from said stationary linear movement unit, it being possible for the first and second sets of linear movement units to be arranged on different sides of the stationary linear movement unit with respect to the linear movement axis.

In accordance with a second inventive concept, the object mentioned at the outset is achieved in constructional terms by a linear movement device comprising at least two linear movement units which are guided in a moveable manner along a shared linear movement axis and comprising a first linear drive and a second linear drive different from the first, in particular for implementing a linear movement device in accordance with the first inventive concept and the developments thereof, the first linear drive being in a movement-transmitting operative connection with a plurality of first rolling means via a first rolling path, each of the at least two linear movement units respectively being connected to at least a first rolling means for the joint linear movement along the linear movement axis, the second linear drive further being in a movement-transmitting operative connection with a plurality of second rolling means via a second rolling path different from the first, each of the at least two linear movement units respectively being connected to at least one of the second rolling means for the joint linear movement along the linear movement axis, it being possible for each rolling path to be set in movement by the linear drive coupled thereto, it being possible for the first rolling means to be set in movement by the first rolling path in an operative connection therewith, it being possible for the second rolling means to be set in movement by the second rolling path in an operative connection therewith, and it being the case for each linear movement unit that the first and the second rolling means respectively connected thereto for joint linear movement are in or can be brought into a predetermined movement relationship relative to one another, in such a way that the first rolling means can be set in movement by the second rolling path and the second rolling means can be set in movement by the first rolling path.

By means of the linear movement device constructed in this manner, in particular the modes of operation and movement disclosed above in accordance with the invention of the linear movement device according to the invention can be achieved.

The first rolling path is a transmission device for directly transmitting drive movement and drive force from the first linear drive to the first rolling means. The second rolling path is a transmission device for directly transmitting drive movement and drive force from the second linear drive to the second rolling means. Since the first and the second rolling means of each linear movement unit are in or can be brought into a predetermined movement relationship relative to one another, for example by means of a coupling, it is possible that on the one hand the first rolling means can be set in movement indirectly via the second rolling means also via the second rolling path and on the other hand the second rolling means can be set in movement indirectly via the first rolling means also via the first rolling path.

Each first rolling means and each second rolling means of a linear movement unit is connected thereto along the linear movement axis for the joint linear movement.

If for example as disclosed above merely one of the two linear drives is activated, whilst the other is deactivated, the rolling means which is in a direct operative connection with the activated linear drive via the associated rolling path is set in movement, the movement thereof being transmitted to the respective other rolling means by way of the predetermined relative movement relationship. This rolls on the other, stationary rolling path. Since the two rolling means are connected to the linear movement unit supporting them for the joint linear movement along the linear movement axis, this rolling movement of the other rolling means on the stationary rolling path leads to a movement of the linear movement unit supporting the two rolling means along the linear movement axis.

Preferably, each rolling path can only be set in movement by the linear drive coupled thereto. As a result, high-precision positioning of the linear movement units along the linear movement axis can be achieved. Preferably, each rolling path can be immobilised independently of the respective other. This can be implemented by way of a brake provided for this purpose or—more preferably—by way of the respective linear drive directly coupled to the rolling path, most simply in that it is or remains deactivated.

Where it is stated in the above that the rolling means are in a movement-transmitting operative connection with the rolling paths, this refers to the possibility of transmitting a relative movement between the respective rolling means and the linear movement unit supporting it and/or to the possibility of transmitting a movement of the rolling means relative to a linear guide of the linear movement units without a relative movement between the rolling means and the linear movement unit supporting it.

One possibility for connecting the first rolling means to a linear movement unit supporting it for the joint linear movement along the linear movement axis, and simultaneously making it possible for the first rolling means to roll on the first rolling path, can be implemented in that a first rolling means, connected to a linear movement unit for joint linear movement, is accommodated about a first axis of rotation, which is immovable relative to the linear movement unit, so as to be rotatable thereabout relative to the linear movement unit.

The equivalent applies to the second rolling means. This can be accommodated about a second axis of rotation, immovable relative to the linear movement unit, so as to be rotatable thereabout relative to the linear movement unit.

"Axis of rotation" means an axis of rotation within the mathematical meaning, in other words an imaginary axis of rotation about which the first and/or the second rolling means can rotate relative to the linear movement unit. The possibility of relative rotation can be achieved in a manner known per se, in that the first and/or the second rolling means is accommodated on the respective linear movement unit thereof so as to be rotatable about an axis fixed with respect to the linear movement unit, as a component in the engineering sense, or in that the first and/or second rolling means comprise(s) a rotation shaft which is mounted so as to be relatively rotatable on the respective linear movement unit.

In a development of the present invention, the first and the second axis of rotation, which are assigned to one and the same linear movement unit, may be arranged mutually parallel at a distance from one another. In this case, a gear unit and/or linkage, which interconnects the first and the second rolling means in the predetermined relative movement relationship, may be provided between the first and the second rolling means. If the rolling means are provided on a linear movement unit so as to be rotatable about the aforementioned axes of rotation, at least one gearwheel or friction wheel may be provided between the first and the second rolling means as a the gear unit for transmitting movement in the predetermined relative movement relationship between the first and the second rolling means of a linear movement unit. If it is desired for the first and the second rolling means always to rotate in the same direction of rotation, an uneven number of movement-transmitting gear unit wheels may be provided between the first and the second rolling means; otherwise, an even number may be provided.

However, in a preferred development of the present invention, a very compact, robust and simple construction can be obtained in that the first and the second axis of rotation of the first and the second rolling means of the same linear movement unit are collinear. In this case, the first and the second rolling means are in direct axial succession in the direction of the shared first and second axis of rotation thereof. To implement the predetermined relative movement relationship, it can be provided, completely generally, that the first and the second rolling means of a linear movement unit are coupled to one another in a predetermined rotational speed transmission ratio as the predetermined relative movement relationship. This can for example be achieved by way of the aforementioned gear unit and/or linkage. However, as is explained in detail below, this can also be achieved by directly coupling the first and the second rolling means of a linear movement unit.

In principle, it is conceivable to implement different rotational speed transmission ratios between the first and the second rolling means of the respective linear movement in different linear movement units. In this case, for example, the same component may always be used as the first rolling means and the same, optionally different, component may be always used as the second rolling means. However, in this case some assembly outlay is required when arranging the movement-transmitting gear unit or linkage between the first and the second rolling means of the respective linear movement unit, since different linear movement units may require different gear units.

It is therefore preferred according to the present invention if the rotational speed transmission ratio is the same in a plurality, preferably in all, of the linear movement units which are connected both to a first and to a second rolling means for joint linear movement. The rotational speed transmission ratio, for example a rotational speed transmission ratio of 1:1, can in this case be achieved simply by directly coupling or by the possibility of directly coupling the first and the second rolling means to one another, and this can be implemented in a simple manner in particular with low construction outlay if the first and the second axis of rotation of the first and the second rolling means are collinear. If it is to be possible, for a given drive of the first and/or the second rolling path, to produce a relative movement between the linear movement units in different linear movement units of the linear movement device, this can be implemented for a rotational speed transmission ratio which is the same for all of the linear movement units in that the first rolling means which are connected to linear movement units for joint linear movement which are directly adjacent in the direction of the linear movement axis have a different circumference, and/or in that the second rolling means which are connected to linear movement units for joint linear movement which are directly adjacent in the direction of the linear movement axis have a different circumference.

In principle, all of the first rolling means of different linear movement units may have the same circumference if the second rolling means of different linear movement units have different circumferences, or the second rolling means of different linear movement units may have the same circumference if the first rolling means of different linear movement units have different circumferences. Preferably, both the first rolling means and the second rolling means of different linear movement units have different circumferences, so as to be able to implement as wide a range as possible of relative speeds between the linear movement units.

For example, the first and the second rolling means of each linear movement unit may be configured as a stepped gearwheel or stepped friction wheel, in other words consist of two wheels of different circumferences or different diameters which are in direct succession along the axis of rotation thereof.

At this point, it should be clarified that each linear movement unit is preferably connected to a different first rolling means and to a different second rolling means from the remainder of the at least two linear movement units for joint movement along the linear movement axis.

So as to be able to implement a positive or negative spreading movement between the at least two linear movement units, in which they are brought further away from or closer to one another, in other words to increase or reduce the distance between two linear movement units which are directly adjacent along the linear movement axis, it may be provided that the circumference of the first rolling means increases in a direction along the linear movement axis from one linear movement unit to the next, directly adjacent linear movement unit. Alternatively or in addition, it may be provided that the circumference of second rolling means decreases from one linear movement unit to the next directly adjacent linear movement unit in a direction, preferably in the same direction as previously for the first rolling means, along the linear movement axis. By combining these two measures, the relative speed which can be achieved between the individual linear movement units can be increased by comparison with implementing merely one of the two aforementioned measures.

In a development of the present invention, the first rolling path and the second rolling part are each a belt, preferably an endlessly circulating belt. In this case, the first and the second rolling means may, as indicated above, each be rolling wheels in direct rolling engagement with one of the belts. To position the linear movement units as precisely as possible, it is preferred, so as to avoid slip between the rolling path and the associated rolling means, if the aforementioned belt is a toothed belt and if the rolling means directly associated with this belt is a gearwheel in meshed engagement with this belt. This applies both to the first and to the second rolling path, and likewise to both the first and the second rolling means.

The first and/or the second rolling path may also be formed by a chain, such as a roller chain.

By selecting the circumferences or diameters of the rolling wheels appropriately for the individual linear movement units, it can be achieved that in individual operation the speed difference between two linear movement units which are directly adjacent along the linear movement axis is equally large for all of the linear movement units. In this way, it can be achieved that in individual operation the linear movement units can be moved towards and away from one another, whilst all of the distances between two linear movement units which are directly adjacent in the direction of the linear movement axis are always the same size for all of the linear movement units if they were the same size at the start of the movement.

Thus, if before the start of operation the linear movement device according to the invention is provided with linear movement units arranged equidistant along the linear movement axis, and the changes in circumference of the first and the second rolling wheels of the respective linear movement units are selected appropriately, the linear movement units will always remain equidistant along the linear movement axis, even if the distance between them increases or decreases.

To increase the number of linear movement units which can be moved by the linear movement device, it may be provided that the linear movement device additionally comprises a first direct linear movement unit, which is directly coupled merely to the first rolling path for joint movement therewith, without rolling means being arranged in between, and/or that it additionally comprises a second direct linear movement unit, which is directly coupled merely to the second rolling path for joint movement therewith, without rolling means being arranged in between.

In this case, the linear movement unit always moves at the same speed at which the rolling path coupled thereto is moved by the associated linear drive. Therefore, the direct linear movement units are preferably arranged as end linear movement units in the direction of the linear movement axis. This means that the direct linear movement unit preferably comprises one of the aforementioned at least two linear movement units as a neighbour on one axial side only, whilst there are no more linear movement units on the opposite axial side. Preferably, if both a first and a second direct linear movement unit are provided, the aforementioned at least two linear movement units are located between the first and the second direct linear movement unit along the linear movement axis.

At this point, it should be clarified that if both ends of a rolling path are rigidly coupled to the direct linear movement unit associated therewith, in such a way that the rolling path comprises an insurmountable obstacle for the linear drive's transmission of drive movement at the fastening point to the direct linear movement unit or the longitudinal ends of the rolling path are even coupled to the direct linear movement unit at an offset orthogonal to the extension direction of said rolling path, the rolling path should still be treated as an endlessly circulating rolling path within the meaning of the present invention.

As was shown above using the specific example of belts and friction wheels or of toothed belts and gearwheels in meshed engagement therewith, the movement-transmitting operative connection, mentioned at the outset, between the first rolling means and the first rolling path and/or between the second rolling means and the second rolling path may be a rolling engagement, in particular a friction-fit rolling engagement or preferably a positive, most preferably meshed rolling engagement.

In principle, the linear movement device according to the invention can still be implemented with exactly two linear movement units (not including any direct linear movement units) even if the decisive advantage thereof only comes into play when more linear movement units are provided with at least a first and at least a second rolling means each as linear drives. Therefore, the linear movement device according to the invention preferably comprises more than two linear movement units, or generally speaking the number of linear movement units which can be driven using two linear drives for individual movement and for block movement is greater or much greater than the number of linear drives provided for driving the movement thereof along the linear movement axis.

So as to be able to bring the linear movement units as close to one another as possible in the axial direction, it may be provided that they comprise more than one linear guide rail extending along the linear movement axis, linear movement units which are in direct succession along the linear movement axis being guided on different linear guide rails.

Unless stated otherwise in individual cases above, "axial" in the present application is always used in relation to the linear movement axis. The "movement" of the linear movement units in the present application is movement relative to coordinate axes which are stationary with respect to a movement guide of the linear movement units.

BRIEF DESCRIPTION OF THE DRAWINGS

The present invention is described in greater detail in the following by way of the accompanying drawings, in which.

DETAILED DESCRIPTION

In the following, reference is made to FIGS. 1, 2 and 3 to describe an embodiment according to the invention of a linear movement device of the present application. However, because of the way the image space is divided up, FIG. 3 probably gives the clearest illustration of the embodiments according to the invention described in the following.

Figure 1:
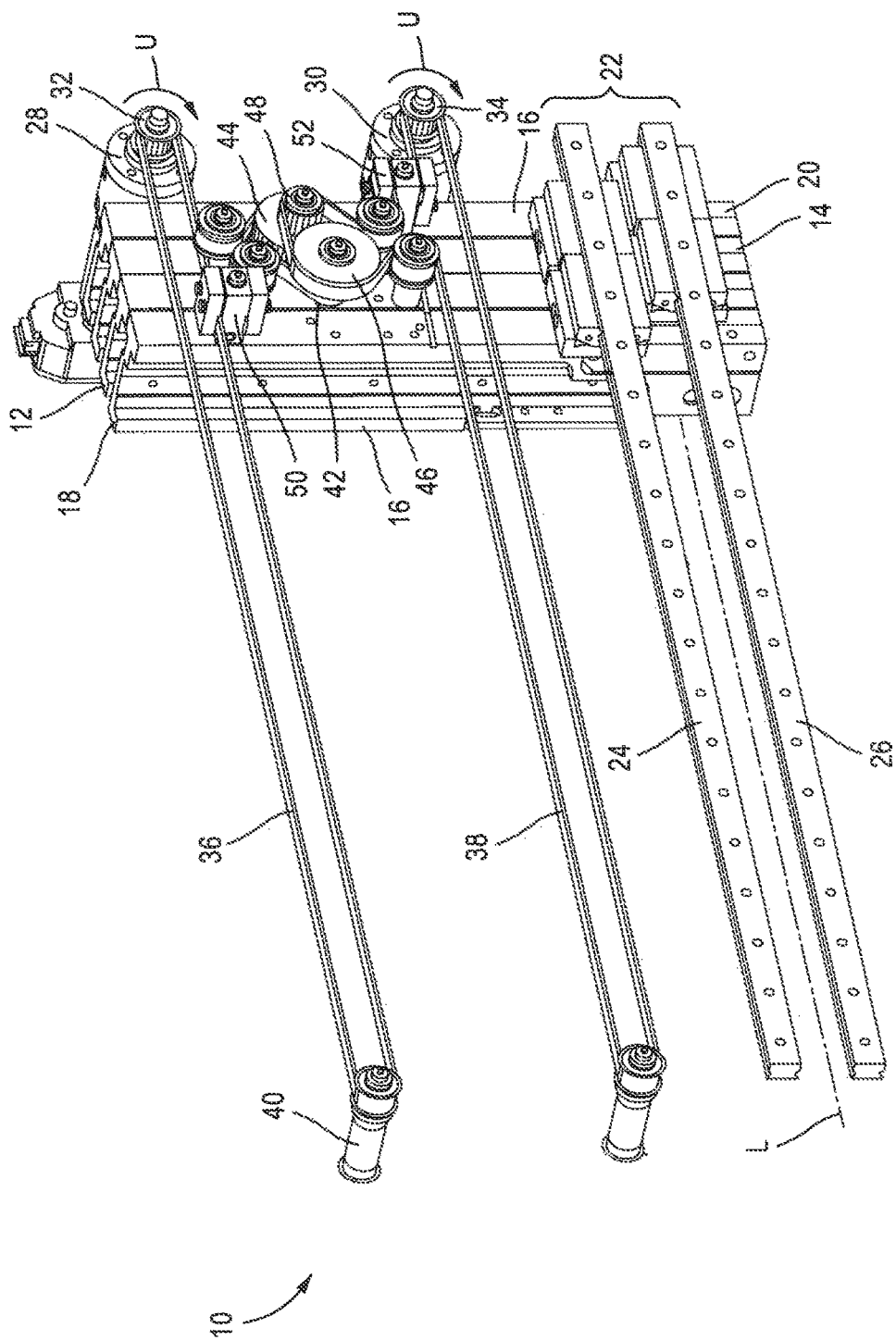
FIG. 1 shows an embodiment of a linear movement device according to the invention in a first extreme position.
Figure 2:
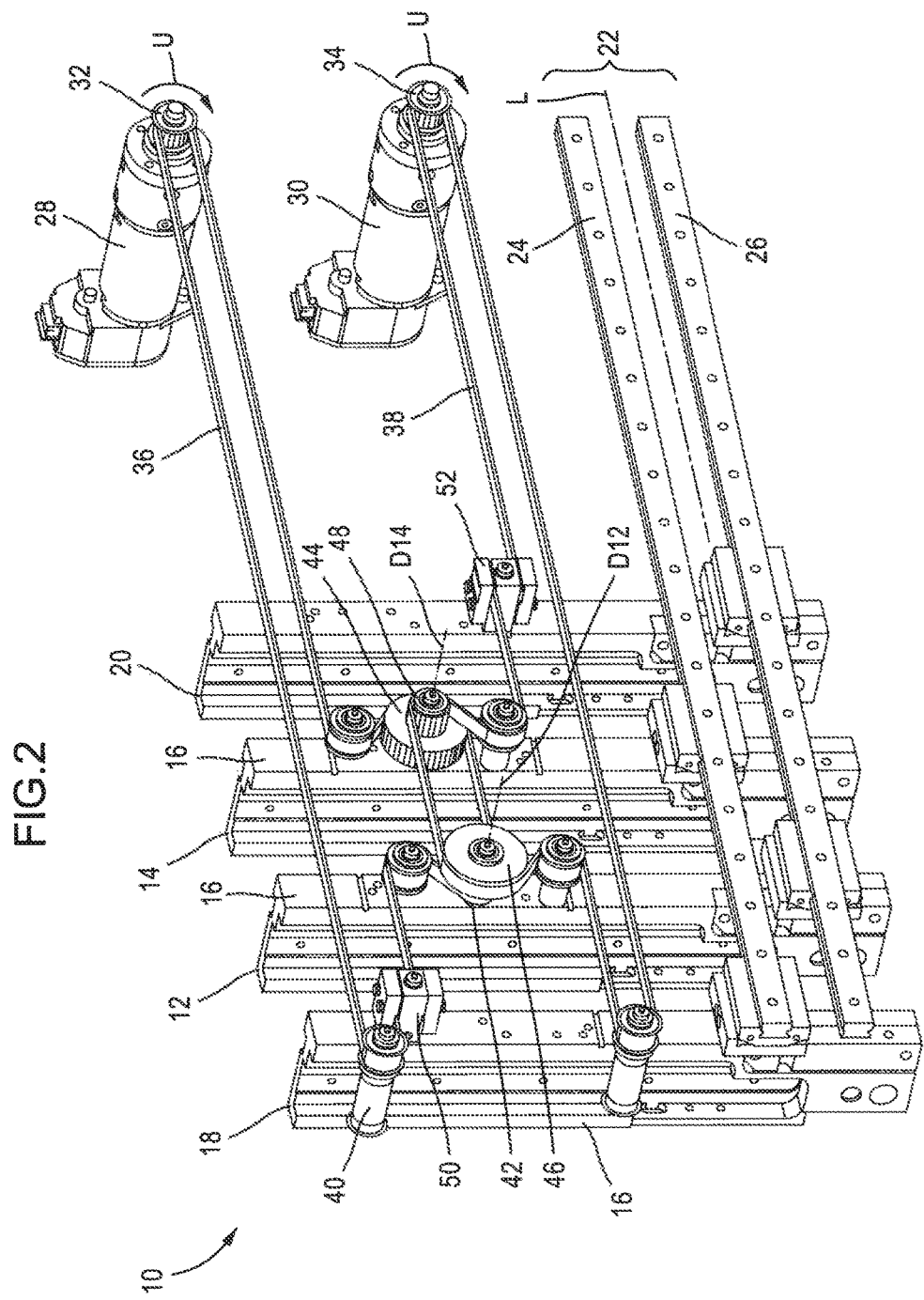
FIG. 2 shows the linear movement device of FIG. 1 in a second operating position.
Figure 3:
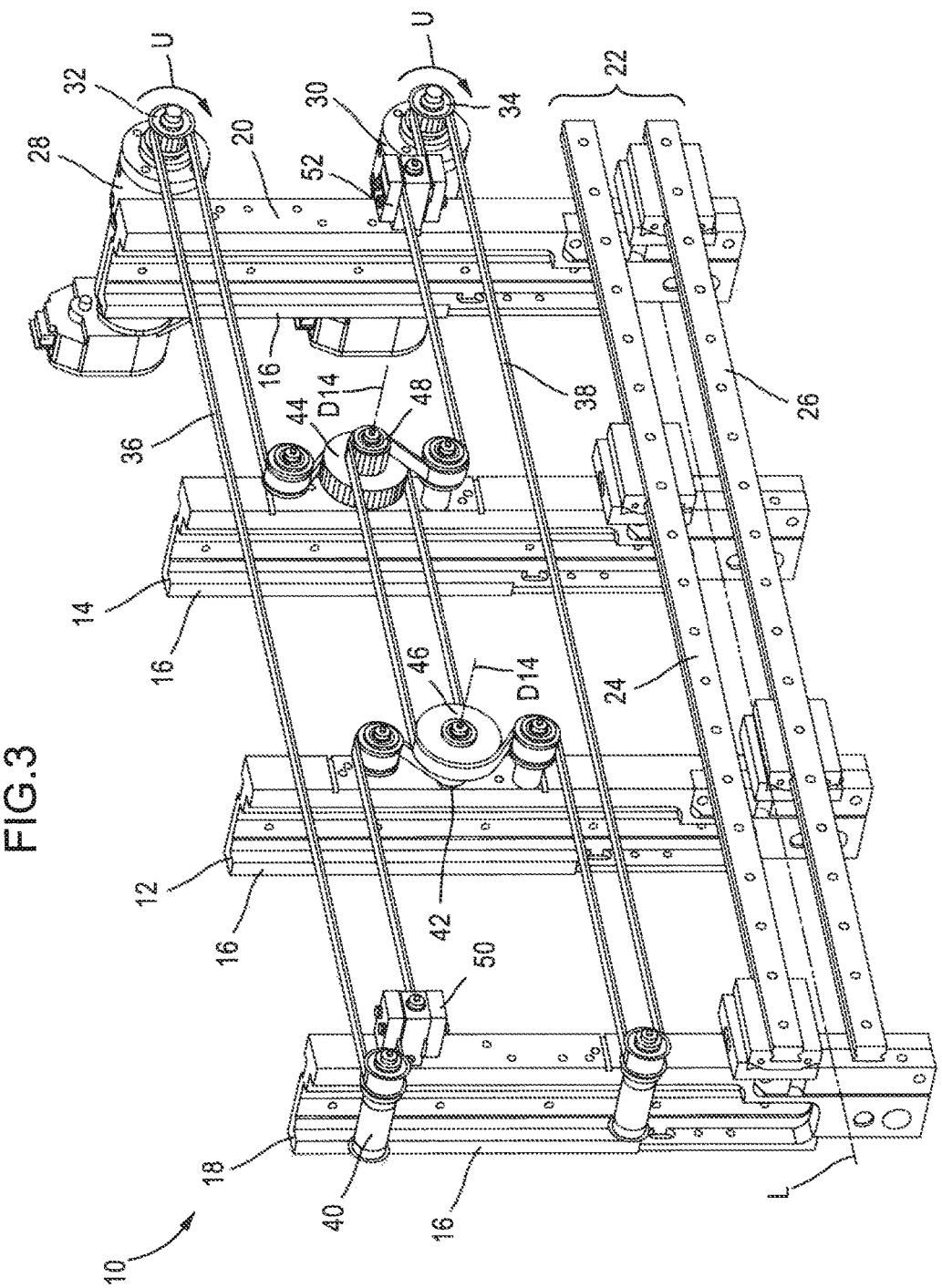
FIG. 3 shows the linear movement device of FIGS. 1 and 2 in the maximally spread operating position.

In FIGS. 1 to 3, a linear movement device according to the invention is denoted as a whole as 10. In the example shown, the linear movement device 10 comprises exactly two linear movement units 12 and 14, two being selected merely for improved clarity. In reality, a linear movement device of the present application will have more than two linear movement units 12 and 14.

The linear movement units 12 and 14 comprise a support 16, formed substantially as a unit, on which for example a pipetting duct of a pipetting device may be accommodated. This duct is not shown in FIGS. 1 to 3, and would extend substantially in the longitudinal direction of the respective support 16, in other words from top to bottom in FIGS. 1 to 3.

In the example shown, the linear movement device 10 further comprises a first direct linear movement unit 18 and a second direct linear movement unit 20, which accommodate the linear movement units 12 and 14 between them. The direct linear movement units 18 and 20 each also comprise a support 16, and serve to accommodate one pipetting duct each in the example shown.

The linear movement units 12 and 14 and the direct linear movement units 18 and 20 are guided in movement along the linear movement axis L on a linear guide 22. The linear guide 22 may comprise two parallel guide rails 24 and 26, on each of which half of the provided linear movement units 12 and 14 and direct linear movement units 18 and 20 can be guided in movement along the linear movement axis L. So as to be able to bring the linear movement units 12 and 14 as close as possible to one another and to the direct linear movement units 18 and 20 axially (in terms of the linear movement axis), directly axially adjacent units of the linear movement units 12 and 14 and direct linear movement units 18 and 20 are preferably guided on different guide rails 24 and 26 in each case. The linear guide 22 further forms a reference point for a coordinate system which is fixed with respect to the guide or frame and by means of which the position and movement of the linear movement units 12 and 14 and direct linear movement units 18 and 20 can be established.

The linear movement device 10 preferably comprises a first linear drive 28 and a second linear drive 30, fixed with respect to the guide or frame. These are preferably electric motors, the drive shafts of which mesh with a toothed belt 36 and a toothed belt 38 respectively via a gearwheel 32 or 34 respectively.

The toothed belt 36 in the embodiment shown is a first rolling path within the meaning of the present application. It is configured as an endlessly circulating toothed belt 36, and is deflected by a return roller 40 at the point thereof axially furthest away from the linear drive 28. The return roller 40, which is fixed with respect to the guide or frame, and the linear drive 28, which is likewise fixed with respect to the guide or frame, between them define the axial displacement path of the linear movement units 12 and 14 and the direct linear movement units 18 and 20.

The toothed belt 36 meshes with a smaller gearwheel 42 on the linear movement unit 12 and meshes with a larger gearwheel 44 on the linear movement unit 14 arranged directly axially adjacent. The size ratios here are selected merely by way of example. Likewise, the gearwheel 42 may be larger and the gearwheel 44 may be smaller. Here, "larger" and "smaller" mean "larger in diameter" or "larger in circumference" and "smaller in diameter" or "smaller in circumference".

The gearwheels 42 and 44 are first rolling means within the meaning of the present invention. They are each connected to the linear movement unit 12 or 14 respectively supporting them so as to be relatively rotatable about a relative rotation axis D12 or D14 but so as only to be able to move jointly axially (in terms of the linear movement axis L). Each gearwheel 42 and 44 can thus rotate about the axis of rotation D12 or D14 on the linear movement unit 12 or 14 respectively supporting it, but can only move jointly along the linear movement axis L with the linear movement unit 12 or 14 respectively supporting it.

The toothed belt 38, which forms a second rolling path within the meaning of the present application, meshes with a gearwheel 46, for example of greater diameter, on the linear movement unit 12 and meshes with a gearwheel 48, for example of smaller diameter, on the directly axially adjacent movement unit 14. The gearwheels 46 and 48 form second rolling means within the meaning of the present application.

The gearwheel 46 is fixed to the linear movement unit 12 supporting it for joint axial movement along the linear movement axis L, but can rotate relative to the linear movement unit 12. Preferably, the axis of rotation of the gearwheel 46 is coaxial with the axis of rotation of the gearwheel 42, in such a way that in the example shown the gearwheel 46 can also rotate about the axis of rotation D12 which is fixed relative to the linear movement unit 12.

The same applies to the gearwheel 48, which can preferably rotate about the axis of rotation D14 which is fixed on the linear movement unit 14, in such a way that the gearwheels 44 and 48 likewise have a coaxial axis of rotation.

The gearwheels of a linear movement unit 12 or 14 which mesh with the toothed belts 36 and 38 are each in a predetermined established relative movement relationship with one another. In the present example, the gearwheels 42 and 46 on the linear movement unit 12 are coupled to one another for joint rotation at the same rotational speed about the axis of rotation D12. Likewise, the gearwheels 44 and 48 on the linear movement unit 14 are coupled to one another for joint rotation at the same rotational speed about the axis of rotation D14.

For the presently selected predetermined relative movement ratio, the first and the second rolling means of a shared linear movement unit may also be formed integrally. For example, the gearwheels 42 and 26, on the one hand, and the gear wheels 44 and 48, on the other hand, could in each case be formed as an integral stepped gearwheel.

Not only can the toothed belts 36 and 38 be driven in movement by the respectively associated linear motors 28 and 30 thereof, but they can preferably also be immobilised, in other words held stationary, by the respectively associated linear drives 28 and 30.

If for example in FIG. 3 the toothed belt 36 is immobilised by the linear drive 28 in a direct drive operative relationship therewith and the drive gearwheel 34 of the linear drive 30 is driven anticlockwise counter to the clockwise direction U, the gearwheels 48 and 46 are each driven in rotation anticlockwise by the toothed belt 38 circulating anticlockwise.

Since in the example shown the gearwheel 44 is coupled to the gearwheel 48 for joint rotation at the same rotational speed and the gearwheel 42 is likewise coupled to the gearwheel 46, these gearwheels 44 and 42 will roll on the immobilised toothed belt 36. As a result of this rolling movement, the linear movement units 12 and 14 will move to the left in FIG. 3, towards an operating position as shown in FIG. 2.

As a result of the selected diameter of the gearwheels 42, 44, 46 and 48 involved, the speed of the linear movement unit 14 to the left will be greater than that of the linear movement unit 12.

The direct linear movement unit 18, which is rigidly directly coupled to the immobilised toothed belt 36 by clamping 50, will be stationary together with the toothed belt 36 relative to the linear guide 22. By contrast, the direct linear movement unit 20 coupled to the toothed belt 38 by the clamping 52 for joint direct movement will be displaced to the left at the same speed as the toothed belt 38.

The diameter of the gearwheel pairings of the gearwheels 42 and 45 on the one hand and 44 and 48 on the other hand are selected in such a way that the speeds of the direct linear movement units and linear movement units in the movement example presently under discussion, from left to right in FIG. 3, increase by the same speed difference. Therefore, the linear movement units 12 and 14 and direct linear movement units 18 and 20, which are arranged equidistant along the linear movement axis L in FIG. 3, remain also always equidistant in the displacement movement thereof presently under discussion, to the left into the position of FIG. 2.

By contrast, if the toothed belt 38 is immobilised by the linear drive 30 directly coupled thereto in a driving operative connection and the linear drive 28 is driven in movement anticlockwise, the direct linear movement unit 18 is driven in movement to the right in FIG. 3 by the moved toothed belt 36 and the gearwheels 42 and 44 are driven in rotation anticlockwise directly by the toothed belt 36. As a result of the above-described relative movement relationship between the gearwheels 42 and 46 on the one hand and 44 and 48 on the other hand, the gearwheel 46 and the gearwheel 48 are also set in rotation in the anticlockwise direction indirectly by the toothed belt 36. The gearwheels 46 and 48 therefore roll on the immobilised toothed belt 38, in such a way that the direct linear movement unit 28 and the linear movement units 12 and 14 are caused to move to the right, until the final position shown in FIG. 1 is eventually reached.

The direct linear movement unit 20 is immobilised with the toothed belt 38 and is stationary in the present movement example. Since the gearwheels 42 and 48 in the example shown are substantially identical and the gearwheels 46 and 44 in the example shown are substantially identical, the movement to the right presently shown, assuming the same movement drive by the linear drive 28 as before, results in the exact same speed distribution as before but inverted: the direct linear movement unit 18 furthest to the left has the same speed as the toothed belt 36 and thus has the greatest axial speed, the linear movement unit 12 has the second greatest, and the linear movement unit 14 has the third greatest, the speed differences between two directly axially adjacent units of the direct linear movement units and linear movement units always being the same size, in such a way that the equidistance between the units advantageously remains preserved during the displacement.

By contrast, if the linear drive 28 is driven anticlockwise and the linear drive 30 is driven clockwise, for example starting from the operating position of FIG. 2, if the appropriate other operating parameters of the linear drives 28 and 30 are selected, the units 18, 12, 14 and 20 can move to the right along the linear movement axis L as a block without any speed relative to one another.

Because of the identical constructions of the gearwheels 42 and 48 on the one hand and 44 and 46 on the other hand and because of the direct coupling of the direct linear movement units 18 and 20 to the toothed belts 36 and 38, in the example shown the toothed belts 36 and 38 have to be driven at the same absolute speed so as to achieve the desired block movement. In this case, the gear wheels 42, 44, 46, 48 do not rotate relative to the linear movement units 12 and 14 supporting them, but are merely move in translation along the linear movement axis L.

Likewise, starting from FIG. 1, by simultaneously driving the linear drive 28 clockwise and the linear drive 30 anticlockwise at the same absolute speed, all of the units 18, 12, 14 and 20 can be moved to the left as a block without any speed relative to one another.

If in the embodiment shown the two linear movement drives are driven in opposite directions at the same time, but not at the same absolute speed, smaller relative speeds between the units 18, 12, 14 and 20 can be set than if one of the toothed belts 36 and 38 were stationary as disclosed above.

Likewise, if in the embodiment shown the two linear drives 28 and 30 are driven in the same direction at the same time, a greater relative speed between the units 18, 12, 14 and 20 can be achieved than if one of the toothed belts 36 and 38 were stationary as disclosed above.

For the linear movement device according to the application, it is advantageous if the first rolling means and the second rolling means consist of two identical sets of different rolling wheels, in particular toothed wheels. This can ensure the equidistance of linear movement units and direct linear movement units during the movement in a simple manner. In this case, the same linear drive can also be used on both rolling paths (preferably toothed belts).

However, if different sets of rolling wheels are used as the first and second rolling means, the above-described operation can be achieved by appropriately selecting different operating parameters of the first and the second linear drive to implement the above-disclosed types of movement.

The transition from the operating position of FIG. 1 to that of FIG. 2 corresponds to a combined block- and spreading movement, since all of the units 18, 12, 14 and 20 move to the left jointly and moreover the distance between them is increased. More precisely, in this case a positive spreading movement is superposed on a block movement.

The transition from the operating position of FIG. 2 to that of FIG. 3 is a pure spreading movement, since the direct linear movement unit 18 remained in place unmoved. More precisely, the movement for the transition from the operating position of FIG. 2 to that of FIG. 3 is a positive spreading movement.

By contrast, to transition from the operating position of FIG. 3 to that of FIG. 1, a negative spreading movement is required, in other words a movement bringing the units 18, 12, 14 and 20 closer to one another. In this case, the direct linear movement unit 20, on the far right in the embodiment shown, remains unmoved.

I claim:

1. A linear movement device comprising:
   at least two linear movement units guided in movement along a shared linear movement axis;
   a first linear drive; and
   a second linear drive;
   wherein each of the at least two linear movement units can be driven in movement along the linear movement axis by at least one of the first linear drive and the second linear drive;
   wherein the first and the second linear drives are coupled to the at least first and second linear movement units so as to transmit drive force so that when only one of the first linear drive and the second linear drive is activated, the at least two linear movement units can be driven in movement in a shared direction along the linear movement axis at different speeds, and when the first and the second linear drives are activated simultaneously, all of the at least two linear movement units can be driven at least in joint movement in the same direction along the linear movement axis at a same speed.

2. The linear movement device according to claim 1, wherein, depending on the respective operating state of the first and second linear drives, at least all but one of the at least two linear movement units can be driven in movement at different speeds along the linear movement axis, or all of the at least two linear movement units can be driven in movement at a same speed along the linear movement axis.

3. The linear movement device according to claim 2, wherein when the first and the second linear drives are activated simultaneously, depending on the respective operating state of the first and second linear drives, all of the at least two linear movement units can be driven in movement at a same speed, or at different speeds, in a shared direction, or a first set of the at least two linear movement units can be driven in movement in a first direction and a second set of the at least two linear movement units can be driven in movement in a second direction counter to the first direction along the linear movement axis.

4. The linear movement device according to claim 1, wherein the linear movement device comprises more than two linear movement units.

5. The linear movement device according to claim 1, wherein the linear movement device comprises more than one linear guide rail extending along the linear movement axis, and wherein linear movement units which are in direct succession along the linear movement axis are guided on different linear guide rails.

6. A linear movement device comprising:
   at least two linear movement units which are guided in a movable manner along a shared linear movement axis;
   a first linear drive; and
   a second linear drive;
   wherein the first linear drive is in a movement-transmitting operative connection with a plurality of first rolling means via a first flexible member;
   wherein each of the at least two linear movement units respectively is connected to at least one of the first rolling means of said first plurality of rolling means for the joint linear movement along the linear movement axis;
   wherein the second linear drive is in a movement-transmitting operative connection with a second plurality of rolling means via a second flexible member;
   wherein each of the at least two linear movement units respectively is connected to at least one of the second plurality of rolling means for the joint linear movement along the linear movement axis;
   wherein each of the first and second flexible members may be set in movement by the linear drive coupled thereto, wherein the first plurality of rolling means may be set in movement by the first flexible member being in operative connection with the first plurality of rolling means, wherein the second plurality of rolling means may be set in movement by the second flexible member being in operative connection with the second plurality of rolling means, wherein the at least one of the first plurality of rolling means and the at least one of the second plurality of rolling means of each linear movement unit are in such a predetermined movement relationship relative to one another that the at least one of the first plurality of rolling means may be set in movement by the second flexible member and that the at least one of the second plurality of rolling means may be set in movement by the first flexible member.

7. The linear movement device according to claim 6, wherein the linear movement device comprises more than two linear movement units.

8. The linear movement device according to claim 6, wherein the linear movement device comprises more than one linear guide rail extending along the linear movement axis, and wherein linear movement units which are in direct succession along the linear movement axis are guided on different linear guide rails.

9. The linear movement device according to claim 6, wherein at least one of the each of the first plurality of rolling means connected to one of the at least two linear movement units for joint linear movement is accommodated so as to be rotatable relative to the one of the at least two linear movement units about a first axis of rotation, said first axis of rotation being immovable relative to the one of the at least two linear movement units.

10. The linear movement device according to claim 9, wherein at least one of the second plurality of rolling means connected to one of the at least two linear movement units for joint linear movement is accommodated so as to be rotatable relative to the one of the at least two linear movement units about a second axis of rotation, said second axis of rotation being immovable relative to the one of the at least two linear movement units.

11. The linear movement device according to claim 10, wherein the first and second axes of rotation are collinear.

12. The linear movement device according to claim 10, wherein the at least one of the first and second plurality of rolling means are coupled to one another in a predetermined rotational speed transmission ratio according to the predetermined relative movement relationship.

13. The linear movement device according to claim 12, wherein a rotational speed transmission ratio is the same in at least two of the at least two linear movement units which are connected both to at least one of the first and to a second plurality of rolling means for joint linear movement.

14. The linear movement device according to claim 12, wherein the rotational speed transmission ratio is 1:1.

15. The linear movement device according to claim 12, wherein the first rolling means of the first plurality of rolling means connected for joint linear movement to the linear movement units that are directly adjacent in the direction of the linear movement axis have different circumferences, and/or the second plurality of rolling means connected for joint linear movement to the linear movement units that are directly adjacent in the direction of the linear movement axis have different circumferences.

16. The linear movement device according to claim 15, wherein the circumferences of the first plurality of rolling means increase in a direction along the linear movement axis from one linear movement unit to the next, directly adjacent linear movement unit, and/or the circumferences of the second plurality of rolling means decrease from one linear movement unit to the next directly adjacent linear movement unit in the same direction along the linear movement axis.

17. The linear movement device according to claim 16, further comprising a first direct linear movement unit, which is directly coupled to the first flexible member for joint movement therewith, without rolling means being arranged in between, and/or further comprising a second direct linear movement unit, which is directly coupled to the second flexible member for joint movement therewith, without rolling means being arranged in between.

18. The linear movement device according to claim 17, wherein a movement-transmitting operative connection between the first plurality of rolling means and the first flexible member and/or between the second plurality of rolling means and the second flexible member is a rolling engagement.

19. The linear movement device according to claim 18, wherein the rolling engagement is a friction-fit rolling engagement or a positive, meshed rolling engagement.

20. The linear movement device according to claim 19, wherein the rolling engagement is a positive, meshed rolling engagement, wherein the first and/or second flexible members are a toothed belt, and the first and/or second plurality of rolling means are gearwheels, which mesh with the toothed belt.

* * * * *